(12) United States Patent
Moorhead et al.

(10) Patent No.: US 6,375,643 B1
(45) Date of Patent: Apr. 23, 2002

(54) URINE/FECAL COLLECTION UNDERGARMENT

(76) Inventors: Kerry Moorhead, 3207 45th St., Lubbock, TX (US) 79413; John Berry, 707 Taylor La., Canyon, TX (US) 79015; Byron Conner, 22306 N. Rebecca Burwell La., Katy, TX (US) 77449

(*) Notice: Subject to any disclaimer, the term of this patent is extended or adjusted under 35 U.S.C. 154(b) by 0 days.

(21) Appl. No.: 09/345,614

(22) Filed: Sep. 14, 1999

(51) Int. Cl.$^7$ ................................................ A61M 1/00
(52) U.S. Cl. ...................... 604/322; 604/348; 604/327; 604/329
(58) Field of Search .................. 604/329, 331, 604/346, 347, 348, 351, 385.19, 385.01, 385.101, 340, 355, 339

(56) References Cited

U.S. PATENT DOCUMENTS

| | | | |
|---|---|---|---|
| 2,277,043 A | * | 3/1942 | Cohn ........................ 128/284 |
| 3,192,926 A | * | 7/1965 | Callaghan .................. 128/286 |
| 3,532,093 A | * | 10/1970 | Lovret ........................ 128/286 |
| 3,626,943 A | * | 12/1971 | Worcester .................. 128/286 |
| 4,122,851 A | * | 10/1978 | Grossner .................... 128/295 |
| 4,200,102 A | * | 4/1980 | Duhamel et al. ........... 128/286 |
| 4,387,726 A | | 6/1983 | Donard |
| 4,453,938 A | | 6/1984 | Brendling |
| 4,457,314 A | | 7/1984 | Knowles |
| 4,640,688 A | | 2/1987 | Hauser |
| 4,661,100 A | | 4/1987 | Rechsteiner |
| 4,675,012 A | | 6/1987 | Rooyakkers |
| 4,690,677 A | | 9/1987 | Erb |
| 4,700,714 A | | 10/1987 | Fuisz |
| 4,743,236 A | | 5/1988 | Manschot |
| 4,752,293 A | | 6/1988 | Smith |
| 4,769,215 A | | 9/1988 | Ehrenkranz |
| 4,784,654 A | | 11/1988 | Beecher |
| 4,840,625 A | | 6/1989 | Bell |
| 4,865,406 A | | 9/1989 | Duran |
| 4,886,509 A | | 12/1989 | Mattsson |
| 4,927,605 A | | 5/1990 | Dorn et al. |
| 5,009,236 A | | 4/1991 | Brothers |
| 5,009,649 A | | 4/1991 | Goulter et al. |
| 5,049,144 A | | 9/1991 | Payton |
| 5,053,027 A | | 10/1991 | Manfredi |
| 5,073,500 A | | 12/1991 | Saito et al. |
| 5,146,637 A | | 9/1992 | Bressler et al. |
| 5,207,663 A | | 5/1993 | McQueen |
| 5,267,988 A | | 12/1993 | Farkas |
| 5,267,990 A | | 12/1993 | Cross et al. |
| 5,269,775 A | | 12/1993 | Freeland et al. |
| 5,318,550 A | | 6/1994 | Cermk et al. |
| 5,334,348 A | | 8/1994 | Saito et al. |
| 5,342,332 A | | 8/1994 | Wheeler |
| 5,387,205 A | | 2/1995 | Cummings |
| 5,388,279 A | | 2/1995 | Rasmussen |
| 5,409,473 A | | 4/1995 | Rosenshein |
| 5,429,624 A | | 7/1995 | Coelho, Jr. |
| 5,462,539 A | | 10/1995 | Herman et al. |
| 5,487,393 A | | 1/1996 | Haswell et al. |
| 5,571,095 A | | 11/1996 | Lu |
| 5,590,648 A | | 1/1997 | Mitchell et al. |
| 5,785,044 A | * | 7/1998 | Meador et al. ............. 128/760 |
| 5,916,202 A | * | 6/1999 | Haswell ...................... 604/356 |
| 6,152,908 A | * | 11/2000 | Widlund et al. ....... 604/385.19 |

* cited by examiner

Primary Examiner—John G. Weiss
Assistant Examiner—Jacqueline Stephens
(74) Attorney, Agent, or Firm—James J. Murphy; Winstead Sechrest & Minick, P.C.

(57) ABSTRACT

The present invention relates to a single use undergarment for use by neonatal, pediatric, adult and geriatric patients for the purposes of obtaining a measured sample of either fecal or urine material. Such devices are needed in order to gather fecal and urine samples in a safe, non-invasive manner without the assistance of medical professionals.

20 Claims, 3 Drawing Sheets

URINE/FECAL COLLECTION UNDERGARMENT

BACKGROUND OF INVENTION

1. Field of Invention

Figure 1:
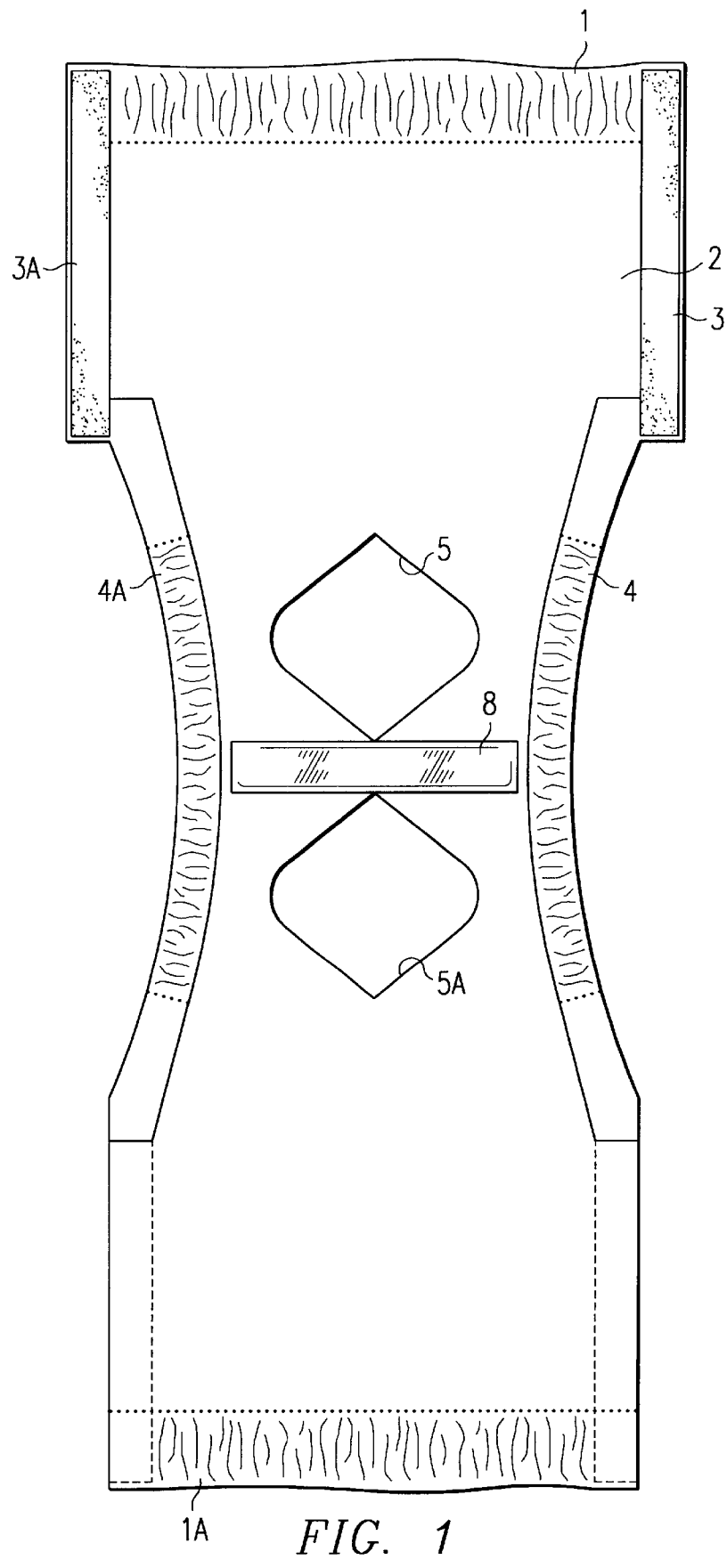

The present invention relates to a single use undergarment for use by neonatal, pediatric, adult and geriatric patients for the purposes of obtaining a measured sample of either fecal or urine material. Such devices are needed in order to gather fecal and urine samples in a safe, non-invasive manner without the assistance of medical professionals.

To provide a safe, non-invasive device for the collection of fecal and urine samples, several problems apparent in the prior art must be addressed. First, the device must be comfortable and thus easily worn in every day situations for the user. Second, the device must provide a manner to collect simultaneous samples of fecal and urine. Third, the samples of fecal and urine collected must be safe from cross contamination, safe from contamination from outside sources, and safe to handle.

2. Description of Prior Art

Devices now commonly used in hospital settings for the purposes of collecting urine and bowel samples for medical testing generally need to be adhesively attached to a patient's genital area causing irritation and are uncomfortable and awkward to wear all of which increases a patient's desire to hold, refrain or restrain from urinating or defecating. When currently marketed devices are full, they most frequently fall off the body unless there is someone there to physically hold the device in the appropriate position for collection. The action of a medical professional physically holding a device to a patient's body inhibits urination as well as defecation.

There is no prior art which allows the simultaneous gathering of fecal and urine samples for the purpose of medical testing. The art that does exist can be placed into one of several categories. First, for patients suffering from urinary incontinence, various forms of absorbent diapers are provided. Examples of such art are U.S. Pat. No. 5,342,332 and U.S. Pat. No. 5,207,6635. U.S. Pat. No. 5,207,663 additionally provides relief for patients suffering from bowel incontinence. The "diapers" disclosed in the afore-referenced art are designed to absorb the fecal or urine discharged from a user. Of course, once the fecal or urine is absorbed, cross-contamination between the samples prevents the samples from being used for the purposes of medical testing. Further, although presumably, the filled diaper material could be squeezed to exhaust urine material, such method would be highly inefficient and allow sample contamination as well as contamination of the medical professional performing the squeezing. Often times watery stool can soak into the diaper leaving an insufficient sample for culture and sensitivity testing. Prolonged or lack of diagnosis can lengthen a patient's required hospital stay.

A second category exists for the collection of urine only in male users which includes some form of a condom type device attached to the penis and connected to a collection reservoir. U.S. Pat. No. 4,387,726 describes such a device. Also included within this category would be devices used to gather urine samples from females which include some form of surface attached to the vaginal area connected through a tube to a collection reservoir. U.S. Pat. No. 5,571,095 is an example of such a device. The attachment to either the penis or the vaginal area is accomplished through various means including adhesion. The adhesion required by this category of urine collection devices can promote irritation as well as discomfort. Devices mentioned above are cumbersome to wear, consequently like the ab-machine that must be pulled down from the attic for use, are generally not regularly used by patients.

A third category of urine and bowel collection devises exist that are not designed to be worn in every day use but rather include cup-like receptacles which are designed to be held. U.S. Pat. No. 3,601,125 is exemplary of this type of device. Obviously, devices in this category cannot be worn by the user and cannot gather fecal and urine samples simultaneously.

SUMMARY OF INVENTION

The urine/fecal collection device of the present invention provides a comfortable device which can be worn in every day use by members of both sexes and of all ages. In particular, the present invention comprises an undergarment formed from an elasticized non-absorbent material, cut to fit and cover from a user's waistline in the front, down across the user's abdomen and genital area; between the legs and up to the user's waistline in the rear, covering both buttocks. The waist band in the front and the rear as well as that portion of the undergarment in contact with a user's legs are formed from an elastic material. The front and rear sections of the undergarment are attached to each other along a user's hips using any means of attachment such as "Velcro"® or adhesive strip. Fenestrations or openings in the undergarment of appropriate size and dimension positioned directly in front of the genital and anal area are used to allow urine and fecal samples to exit the undergarment and be collected.

In order to prevent cross contamination between fecal and urine samples, a strip of non-absorbent material referred to as a gel dam, is attached to the elasticized non-absorbent undergarment between the genital fenestration and the anal fenestration. Samples are collected in a collection bag composed of upper and lower portions; the upper and lower portions further divided into a fecal collection section and a urine collection section. The collection bag is of a size and shape that will allow the bag to be suspended comfortably between a user's legs. The inlet to the upper portion of the urine collection section of the collection bag is attached to the genitalia fenestration while the upper portion of the fecal collection section of the collection bag is attached to the anal fenestration.

Fecal or urine samples are designed by the present invention to pass through the upper portion and be deposited in the lower portion of the collection bag. Once filled with a sample, the lower portions of the collection bag can be torn away from the upper portion and both portions sealed through the use of any conventional means such as that existing in the common "Ziplock"® bag. The fecal collection lower portion can also be separated from the urine collection lower portion of the collection bag.

It is an object of the present invention to provide a urine/fecal collection device that allows a patient or user to move freely about thereby reducing the feelings of restriction associated with the use of prior art devices.

It is a further object of the present invention to provide a comfortable, natural feeling undergarment which can be used by neonates, infants, young children, adults, elderly, incapacitated and bed ridden patients of both sexes.

It is still a further object of the present invention to provide a time saving device which allows medical professionals to collect urine and fecal samples without physically holding the sampling device. Additionally, the present invention is simple to use which will allow non-medical

BRIEF DESCRIPTION OF THE INVENTION

Figure 2:
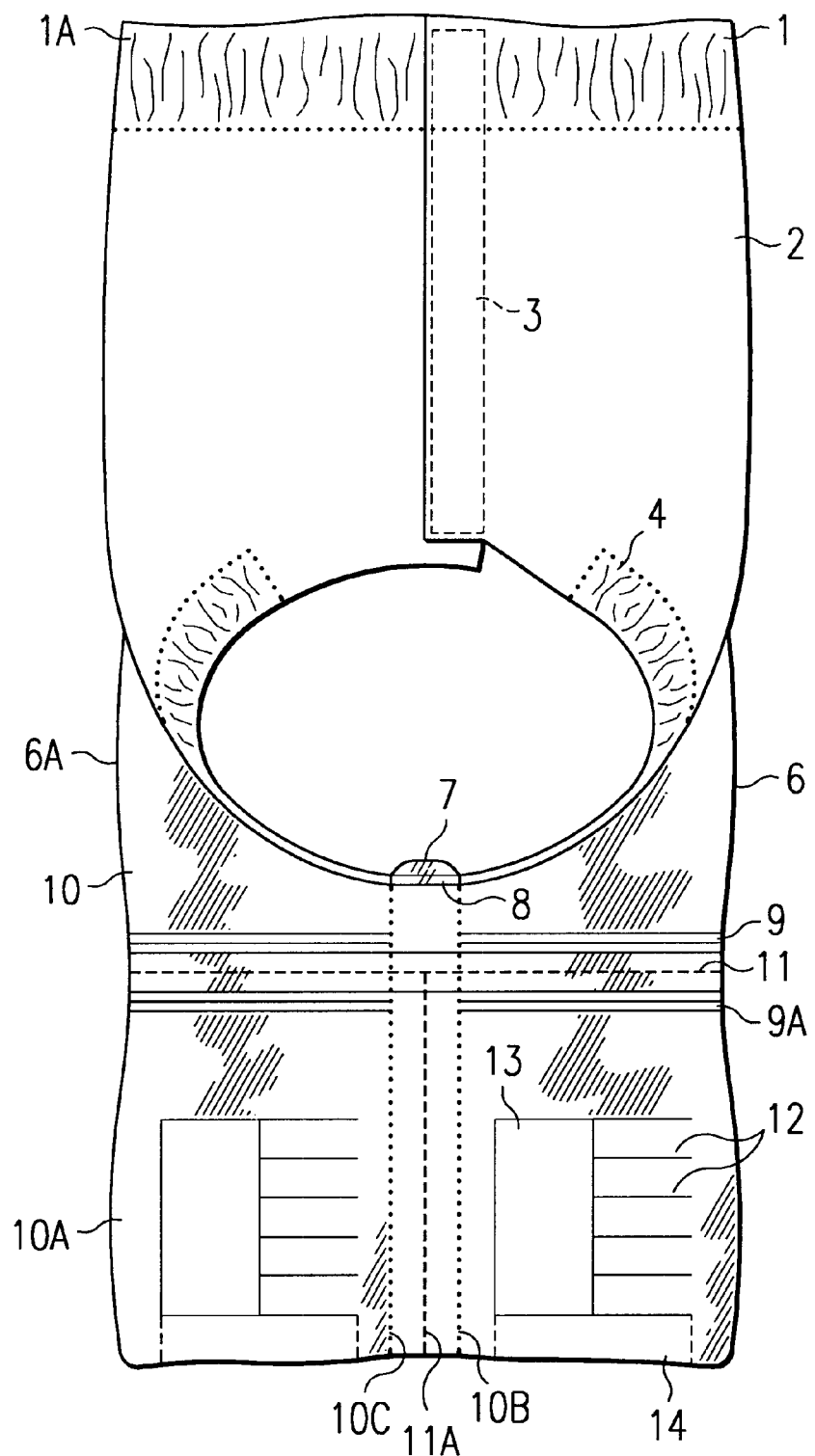
Figure 3:
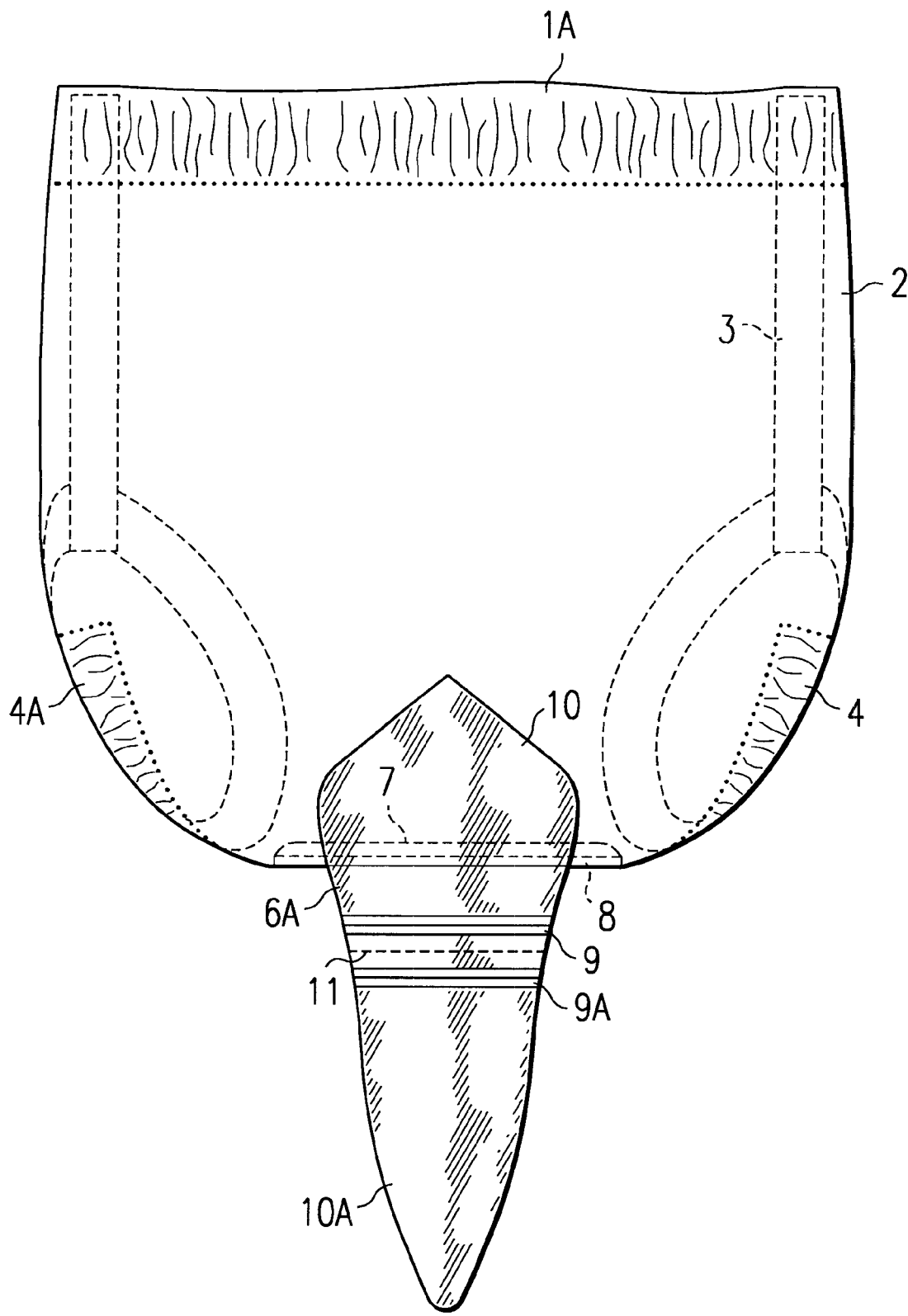

FIG. 1 depicts a plan view of the present invention;

FIG. 2 details a side view of the present invention, wherein the garment of FIG. 1 has been folded into a wearing configuration and rotated ninety degrees with respects to the view of FIG. 1; and FIG. 3 depicts a front view of the present invention.

DETAILED DESCRIPTION OF THE INVENTION

FIG. 1 shows a plan view of the present invention. The Urine/Fecal Collection Undergarment ("UFCU") is made from constructing an undergarment in the general shape of a "diaper" from any elasticized non-absorbent material (2). The UFCU can be of any size ranging from a size designed to fit an infant male/female to that designed to fit an adult man/woman. An elastic waist band is attached to the UFCU at the top and bottom, at that portion of the UFCU designed to fit around the waistline of a person (1 and 1A). The elastic waistband (1 and 1A) can be made of any elastic material. While any means of attachment can be used to fasten the ends of the elastic waistband (1 and 1A) together), FIG. 1 shows the use of either "Velcro"® or adhesive tape (3 and 3A). Around the leg entry portion of the UFCU are leg closures (4 and 4A) made of material that when worn causes the leg closures to fit tightly and securely to an individual's legs. The leg closures (4 and 4A) can be made of any material which is elastic in nature. Two fenestrations (5 and 5A) or openings are located on the UFCU which allow the flow of feces or urine into, as shown on FIG. 2, the urine collection bag (6) or the fecal collection bag (6A). Although FIG. 2 depicts booth a urine (6) and fecal (6A) collection bag, the UFCU can be made with either just a urine collection bag or a fecal collection bag. The fenestrations (5 and 5A) are located on the UFCU at an area anatomically beneath the general vicinity of where a person's penis/vagina and anus would be situated. To prevent the flow of fecal material into the urine collections bag and vice versa, the two fenestrations (5 and 5A) are separated by gel dam (7) made of soft, water insoluble material such as silicone. The gel dam is supported (7A) by any convention means of support such as plastic.

FIG. 2 details a side view of the UFCU as assembled for wearing. The plastic waist band can again be seen (1 and 1A) as joined by the adhesive closure (3). Although only one adhesive closure is seen on FIG. 2, a similar adhesive closure (3A) would exist on the opposite side of the UFCU. The leg closures (4 and 4A) are shown on FIG. 2.

FIG. 2 depicts the urine (6) and fecal (6A) collection bags as attached to the UFCU. Any means of attachment can be used to attach the urine (6) and fecal (6A) collection bags to the UFCU such as heat, glue or ultrasound. The urine (6) and fecal (6A) collections bags can be of any size, however, a size that is comfortable extending downward from a person's buttock and between a person's legs is the most desirable. Furthermore, the urine (6) and fecal (6A) collections bags can be made of any material that will hold liquids or solids, although the present invention utilizes collection bags made of clear, playable, plastic such as that used in common "Ziplock"® bags.

The urine (6) and fecal (6A) collection bags contain an upper (10) and lower (10A) portion which is separated by an upper (9) and lower (9A) sealing means. The sealing means can be any means which will allow a water tight seal at the position shown such as the interlocking means utilized in common "Ziplock" bags. Around the circumference of the urine (6) and fecal (6A) collections bags, between the upper (9) and lower (9A) sealing means is a slightly perforated line (11). Once urine or feces flows through the upper portion (10) into the lower portion (10A) of the urine (6) or fecal (6A) collections bags, the upper (9) and lower (9A) sealing means can be sealed and the lower (10A) portion of the collection bag separated from the upper (10) portion, along with the slightly perforated line (11).

The urine (6) and fecal (6A) collection bags are isolated from each other by seams 10B and 10C formed by any conventional means such as glue, heat or ultrasound. Another slightly perforated line (11A) which will allow the fecal collection bag to be separated from the urine collection bag, extends between the seams 10B and 10C from the bottom of the collection bags to the first sealing means (9). Although not essential to the function of the UFCU, FIG. 2 depicts urine (6) and fecal (6A) collection bags with liquid graduations (12), a frosted note area (13) and a location for writing the tear weight of the collation bags (14).

FIG. 3 shows a front view of the UFCU as assembled for wear. Again shown on FIG. 3 is the elastic waist band (1 and 1A) attached by the adhesive closure (3) and the leg closures (4 and 4A). The urine (6) and collections bag is shown on FIG. 3 along with the upper (9) sealing means.

While the invention has been described with reference to certain preferred characteristics, those skilled in the art will appreciate that certain changes and modifications can be made without departing form the scoop and spirit of the Invention as defined by the following claims.

We claim:

1. A elasticized form-fitting urine/fecal collection undergarment comprising an undergarment made from non-absorbent elastic material, of suitable size and shape to fit and cover a user's waistline in the front, down across the user's abdomen and genital area; between the legs and up to the user's waistline in the rear, covering both buttocks; two fenestrations located anatomically beneath the general vicinity where a user's genital area and anal area would be situated; and independently removable urine and fecal collection bags attached to the urine/fecal collection undergarment.

2. The urine/fecal collection undergarment as in claim 1 further comprising a gel dam between the two fenestrations.

3. The urine/fecal collection undergarment as in claim 2 wherein a means of support is located beneath the gel dam.

4. The urine/fecal collection undergarment as in claim 2 where the gel dam is made from water insoluble material.

5. The urine/fecal collection undergarment as in claim 3 where the gel dam support means is made from plastic or plastic like material.

6. The urine/fecal collection undergarment as in claim 1 wherein the urine and fecal collection bags contain an upper portion and lower portion.

7. The urine/fecal collection undergarment as in claim 6 wherein the upper portion and lower portion of the urine and fecal collection bags are separated by a sealing means located at the bottom of the upper portion and top of the lower portion.

8. The urine/fecal collection undergarment as in claim 7 wherein a slightly perforated line extends around the circumference of the urine and fecal collection bags between the sealing means.

9. The urine/fecal collection undergarment as in claim 8 wherein the sealing means is an interlocking means such as that used in common sealable plastic bags.

10. The urine/fecal collection undergarment as in claim 8 where a slightly perforated line extends between the urine and fecal collection bags from the bottom of such bags to the lower sealing means.

11. A elasticized form-fitting urine collection undergarment comprising an undergarment made from non-absorbent elastic material, of suitable size and shape to fit and cover a user's waistline in the front, down across the user's abdomen and genital area; between the legs and up to the user's waistline in the rear, covering both buttocks; a fenestration located anatomically beneath the general vicinity where a user's genital area would be situated; and an independently removable urine collection bag is attached to the urine collection undergarment.

12. The urine collection undergarment as in claim 11 wherein the urine collection bag contains an upper portion and lower portion.

13. The urine collection undergarment as in claim 12 wherein the upper portion and lower portion of the urine collection bag is separated by a sealing means located at the bottom of the upper portion and top of the lower portion.

14. The urine collection undergarment as in claim 13 wherein a slightly perforated line extends around the circumference of the urine collection bag between the sealing means.

15. The urine collection undergarment as in claim 14 wherein the sealing means is an interlocking means such as that used in common sealable plastic bags.

16. A an elasticized form-fitting fecal collection undergarment comprising undergarment made from non-absorbent elastic material, of suitable size and shape to fit and cover a user's waistline in the front, down across the user's abdomen and genital area; between the legs and up to the user's waistline in the rear, covering both buttocks; a fenestration located anatomically beneath the general vicinity where a users anal area would be situated; and an independently removable fecal collection bag is attached to the fecal collection undergarment.

17. The fecal collection undergarment as in claim 16 wherein the fecal collection bag contains an upper portion and lower portion.

18. The fecal collection undergarment as in claim 17 wherein the upper portion and lower portion of the fecal collection bag is separated by a sealing means located at the bottom of the upper portion and top of the lower portion.

19. The fecal collection undergarment as in claim 18 wherein a slightly perforated line extends around the circumference of the fecal collection bag between the sealing means.

20. The fecal collection undergarment as in claim 19 wherein the sealing means is an interlocking means such as that used in common sealable plastic bags.

\* \* \* \* \*